United States Patent
Solem et al.

(10) Patent No.: US 7,044,967 B1
(45) Date of Patent: May 16, 2006

(54) DEVICE AND METHOD FOR TREATMENT OF MITRAL INSUFFICIENCY

(75) Inventors: Jan Otto Solem, Stetten (CH); Per Ola Kimblad, Lund (SE)

(73) Assignee: Edwards Lifesciences AG, Saint-Prex (CH)

( * ) Notice: Subject to any disclaimer, the term of this patent is extended or adjusted under 35 U.S.C. 154(b) by 0 days.

(21) Appl. No.: 10/019,563

(22) PCT Filed: Jun. 28, 2000

(86) PCT No.: PCT/SE00/01369

§ 371 (c)(1),
(2), (4) Date: Jul. 1, 2002

(87) PCT Pub. No.: WO01/00111

PCT Pub. Date: Jan. 4, 2001

(30) Foreign Application Priority Data

Jun. 29, 1999 (SE) .................................. 9902455

(51) Int. Cl.
*A61F 2/06* (2006.01)

(52) U.S. Cl. ..................................... 623/2.36; 623/903

(58) Field of Classification Search ...... 623/2.36–2.37, 623/2.42, 904, 2.11, 1.11–1.15, 903
See application file for complete search history.

(56) References Cited

U.S. PATENT DOCUMENTS

| | | |
|---|---|---|
| 4,164,046 A | 8/1979 | Cooley |
| 4,655,771 A | 4/1987 | Wallsten |
| 4,954,126 A | 9/1990 | Wallsten |
| 5,006,106 A | 4/1991 | Angelchik |
| 5,061,275 A | 10/1991 | Wallsten et al. |
| 5,064,435 A | 11/1991 | Porter |
| 5,104,404 A * | 4/1992 | Wolff .......................... 623/1.16 |
| 5,170,802 A * | 12/1992 | Mehra .......................... 607/126 |
| 5,383,892 A | 1/1995 | Cardon et al. |
| 5,476,471 A | 12/1995 | Shifrin et al. |
| 5,534,007 A | 7/1996 | St. Germain et al. |
| 5,571,135 A | 11/1996 | Fraser et al. |
| 5,584,879 A | 12/1996 | Reimold et al. |
| 5,591,197 A * | 1/1997 | Orth et al. .................. 623/1.16 |
| 5,593,442 A * | 1/1997 | Klein ........................ 623/23.64 |
| 5,674,280 A | 10/1997 | Davidson et al. |
| 5,713,949 A | 2/1998 | Jayaraman |

(Continued)

FOREIGN PATENT DOCUMENTS

DE 196 05 042 A1 1/1998

(Continued)

OTHER PUBLICATIONS

Circumferential Suture of the Mitral Annulus for Correction of Mitral Regurgitation in Dogs by Buchanan JW, Sammarco CD Vet Surg. May-Jun. 1998; 27(3); 182-93.*

(Continued)

*Primary Examiner*—Suzette J-J Gherbi
(74) *Attorney, Agent, or Firm*—David L. Hauser (57) ABSTRACT

A device for treatment of mitral annulus dilatation comprises an elongate body having two states. In a first of these states the elongate body is insertable into the coronary sinus and has a shape adapting to the shape of the coronary sinus. When positioned in the coronary sinus, the elongate body is transferable to the second state assuming a reduced radius of curvature, whereby the radius of curvature of the coronary sinus and the radius of curvature as well as the circumference of the mitral annulus is reduced.

27 Claims, 5 Drawing Sheets

U.S. PATENT DOCUMENTS

| | | | |
|---|---|---|---|
| 5,741,274 A | 4/1998 | Lenker et al. | |
| 5,817,126 A * | 10/1998 | Imran | 623/1.15 |
| 5,824,071 A | 10/1998 | Nelson et al. | |
| 5,876,419 A | 3/1999 | Carpenter et al. | |
| 5,911,732 A | 6/1999 | Hojeibane | |
| 5,919,233 A | 7/1999 | Knopf et al. | |
| 5,980,552 A | 11/1999 | Pinchasik et al. | |
| 6,027,525 A | 2/2000 | Suh et al. | |
| 6,093,203 A | 7/2000 | Uflacker | |
| 6,183,411 B1 | 2/2001 | Mortier et al. | |
| 6,203,556 B1 | 3/2001 | Evans et al. | |
| 6,210,432 B1 * | 4/2001 | Solem et al. | 623/1.15 |
| 6,221,103 B1 | 4/2001 | Melvin | |
| 6,248,119 B1 | 6/2001 | Solem | |
| 6,250,308 B1 * | 6/2001 | Cox | 128/898 |
| 6,264,602 B1 | 7/2001 | Mortier et al. | |
| 6,264,691 B1 | 7/2001 | Gabbay | |
| 6,325,826 B1 | 12/2001 | Vardi et al. | |
| 6,343,605 B1 | 2/2002 | Lafontaine | |
| 6,350,277 B1 | 2/2002 | Kocur | |
| 6,402,679 B1 | 6/2002 | Mortier et al. | |
| 6,402,680 B1 | 6/2002 | Mortier et al. | |
| 6,402,781 B1 * | 6/2002 | Langberg et al. | 623/2.36 |
| 6,409,760 B1 | 6/2002 | Melvin | |
| 6,537,314 B1 * | 3/2003 | Langberg et al. | 623/2.36 |
| 6,569,198 B1 | 5/2003 | Wilson et al. | |
| 6,626,899 B1 | 9/2003 | Houser et al. | |
| 6,656,221 B1 | 12/2003 | Taylor et al. | |
| 6,669,687 B1 | 12/2003 | Saadat | |
| 6,706,065 B1 | 3/2004 | Langberg et al. | |
| 6,709,456 B1 | 3/2004 | Langberg et al. | |
| 6,790,231 B1 | 9/2004 | Liddicoat et al. | |
| 6,824,562 B1 | 11/2004 | Mathis et al. | |
| 6,908,478 B1 * | 6/2005 | Alferness et al. | 623/1.11 |
| 2001/0044568 A1 | 11/2001 | Langberg et al. | |
| 2002/0016628 A1 | 2/2002 | Langberg et al. | |
| 2002/0019660 A1 | 2/2002 | Gianoui et al. | |
| 2002/0022880 A1 | 2/2002 | Melvin | |
| 2002/0087173 A1 | 7/2002 | Alferness et al. | |
| 2002/0103532 A1 | 8/2002 | Langberg et al. | |
| 2002/0103533 A1 | 8/2002 | Langberg et al. | |
| 2002/0111533 A1 | 8/2002 | Melvin | |
| 2002/0124857 A1 | 9/2002 | Schroeppel | |
| 2002/0151961 A1 | 10/2002 | Lashinski et al. | |
| 2003/0212453 A1 * | 11/2003 | Mathis et al. | 623/2.11 |
| 2004/0133192 A1 | 7/2004 | Houser et al. | |
| 2004/0153146 A1 | 8/2004 | Lashinski et al. | |

FOREIGN PATENT DOCUMENTS

| | | |
|---|---|---|
| DE | 196 11 755 A1 | 2/1998 |
| EP | 0 727 239 A2 | 8/1996 |
| WO | WO 95/16407 | 6/1995 |
| WO | WO 96/40356 | 12/1996 |
| WO | WO 98/18411 | 5/1998 |
| WO | WO 99/44534 | 9/1999 |
| WO | WO 99/53977 | 10/1999 |
| WO | WO 00/18320 | 4/2000 |
| WO | WO 00/41649 | 7/2000 |
| WO | WO 00/44313 A1 | 8/2000 |
| WO | WO 01/00111 A1 | 1/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/50888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |

OTHER PUBLICATIONS

Laaksovirta et al., *Expansion and bioabsorption of the self-reinforced lactic and glycolic acid copolymer prostatic spiral stent*, PubMed, Excerpt from J Urol 2001 Sep.; 166(3):919-22, one sheet.

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in dentistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2):101-4, one sheet.

Kuo et al., *The use of nickel-titanium alloy in orthopedic surgery in China*, PubMed, Excerpt from Orthopedics Jan. 1989; 12(1);111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/7906notw1.html, News of the Week Materials, Feb. 5, 2001, vol. 79, No. 6, Cenear 79 6 pp.5, ISSN 0009-2347, Mairin Brennan, three sheets.

Stikeman, *Total Recall*, Technology Review—Innovation: Total Recall, An MIT Enterprise Technology Review, Jun. 2001, two sheets.

European Patent Office Office action dated Dec. 22, 2003 for Application No. 00 946 661.6-2310.

Written Opinion dated Nov. 8, 2002 for International application No. PCT/EP01/10371.

International Search Report dated Apr. 23, 2002 for International application No PCT/EP01/10371.

International Search Report dated Mar. 15, 2000.

International Search Report dated Oct. 9, 2002 for National application No. 0200073-5.

International Search Report dated Jun. 5, 2003 for International application No. PCT/EP02/14655.

Buchanan et al., Circumferential Sutute of the Mitral Annulus for Correction of Mitral Regurgitation in Dogs, Veterinary Surgery, 27: 182-193, 1998.

Buchanan JW, Sammarco CD, Circumferential Suture of the Mitral Annulus for Correction of Mitral Regurgitation in Dogs, PubMed, Excerpt from Vet Surg May-Jun. 1998; 27(3): 183-93, abstract, one sheet.

* cited by examiner

DEVICE AND METHOD FOR TREATMENT OF MITRAL INSUFFICIENCY

REFERENCE TO RELATED APPLICATIONS

The present application is the national stage under 35 U.S.C. 371 of international application PCT/SE00/01369, filed Jun. 28, 2000 which designated the United States, and which international application was published under PCT Article 21(2) in the English language. The present application is a continuation of U.S. patent application Ser. No. 09/345,475 filed Jun. 30, 1999, now U.S. Pat. No. 6,210,432, issued Apr. 3, 2001.

FIELD OF THE INVENTION

The present invention generally relates to a device and a method for treatment of mitral insufficiency and, more specifically, for treatment of dilatation of the mitral annulus.

BACKGROUND

Mitral insufficiency can result from several causes, such as ischemic disease, degenerative disease of the mitral apparatus, rheumatic fever, endocarditis, congenital heart disease and cardiomyopathy. The four major structural components of the mitral valve are the annulus, the two leaflets, the chordae and the papillary muscles. Any one or all of these in different combinations may be injured and create insufficiency. Annular dilatation is a major component in the pathology of mitral insufficiency regardless of cause. Moreover, many patients have a mitral insufficiency primarily or only due to posterior annular dilatation, since the annulus of the anterior leaflet does not dilatate because it is anchored to the fibrous skeleton of the base of the heart.

Studies of the natural history of mitral insufficiency have found that totally asymptomatic patients with severe mitral insufficiency usually progress to severe disability within five years. At present the treatment consists of either mitral valve replacements or repair, both methods requiring open heart surgery. Replacement can be performed with either mechanical or biological valves.

The mechanical valve carries the risk of thromboembolism and requires anticoagulation, with all its potential hazards, whereas biological prostheses suffer from limited durability. Another hazard with replacement is the risk of endocarditis. These risks and other valve related complications are greatly diminished with valve repair.

Mitral valve repair is theoretically possible if an essentially normal anterior leaflet is present. The basic four techniques of repair include the use of an annuloplasty ring, quadrangular segmental resection of diseased posterior leaflet, shortening of elongated chordae, and transposition of posterior leaflet chordae to the anterior leaflet.

Annuloplasty rings are needed to achieve a durable reduction of the annular dilatation. All the common rings are sutured along the posterior mitral leaflet adjacent to the mitral annulus in the left atrium. The Duran ring encircles the valve completely, whereas the others are open towards the anterior leaflet. The ring can either be rigid, like the original Carpentier ring, or flexible but non-elastic, like the Duran ring or the Cosgrove-Edwards ring.

Effective treatment of mitral insufficiency currently requires open-heart surgery, by the use of total cardiopulmonary by-pass, aortic cross-clamping and cardioplegic arrest.

To certain groups of patient, this is particular hazardous. Elderly patients, patients with a poor left ventricular function, renal disease, severe calcification of the aorta, previous cardiac surgery or other concomitant diseases, would in particular most likely benefit from a less invasive approach, even if repair is not complete. The current trend towards less invasive coronary artery surgery, without cardiopulmonary by-pass, as well as PTCA will also call for a development of a less invasive method for repair of the often concomitant mitral insufficiency.

SUMMARY

A first object of the present invention is to provide a device and a method for treatment of mitral insufficiency without the need for cardiopulmonary by-pass and opening of the chest and heart.

A second object of the invention is to provide reduction of the mitral annulus using less invasive surgery.

According to the present invention, a device for treatment of mitralis insufficiency comprises an elongate body having such dimensions as to be insertable into the coronary sinus and having two states, in a first state of which the elongate body has a shape that is adaptable to the shape of the coronary sinus, and to the second state of which the elongate body is transferable from the said first state assuming a reduced radius of curvature, whereby the radius of curvature of the coronary sinus is reduced as well as the circumference of the mitral valve annulus, when the elongate body is positioned in the coronary sinus.

Preferably, means are provided for the transfer of the elongate body to the second state by bending and/or shortening it from a larger radius of curvature to a smaller radius of curvature.

The transfer means may comprise-means for bending and/or shortening the elongate body by a preferably asymmetric contraction thereof.

Further, the elongate body may comprise a memory material providing the transfer to the second state.

In a preferred embodiment, the elongate body may comprise a stent. In an alternative embodiment, the device according to the invention may comprise several stent sections and said bending and/or shortening means may comprise wires for shortening the distance between the stent sections.

According to a second aspect, a method of reducing the circumference of the mitral valve annulus comprises the steps of inserting an elongate body into the coronary sinus in the vicinity of the posterior leaflet of the mitral valve, and then providing a bending and/or shortening of the elongate body when positioned in the coronary sinus so as to reduce the curvature of the coronary sinus and thereby reduce the circumference of the mitral valve annulus.

Thus, the present invention takes advantage of the position of the coronary sinus being close to the mitral annulus. This makes repair possible by the use of current catheter-guided techniques.

The coronary veins drain blood from the myocardium to the right atrium. The smaller veins drain blood directly into the atrial cavity, and the larger veins accompany the major arteries and run into the coronary sinus which substantially encircles the mitral orifice and annulus. It runs in the posterior atrioventricular groove, lying in the fatty tissue between the left atrial wall and the ventricular myocardium, before draining into the right atrium between the atrial septum and the post-Eustachian sinus.

In an adult, the course of the coronary sinus may approach within 5–15 mm of the medial attachment of the posterior leaflet of the mitral valve. Preliminary measurements performed at autopsies of adults of normal weight show similar results, with a distance of 5.3±0.6 mm at the medial attachment and about 10 mm at the lateral aspect of the posterior leaflet. The circumference of the coronary sinus was 18.3±2.9 mm at its ostium (giving a diameter of the posterior leaflet of 5.8±0.9 mm) and 9.7±0.6 mm along the lateral aspect of the posterior leaflet (corresponding to a diameter of 3.1±0.2 mm).

BRIEF DESCRIPTION OF THE DRAWINGS

The invention will be better understood by the following description of preferred embodiments referring to the appended drawings, in which.

DETAILED DESCRIPTION

Figure 1:
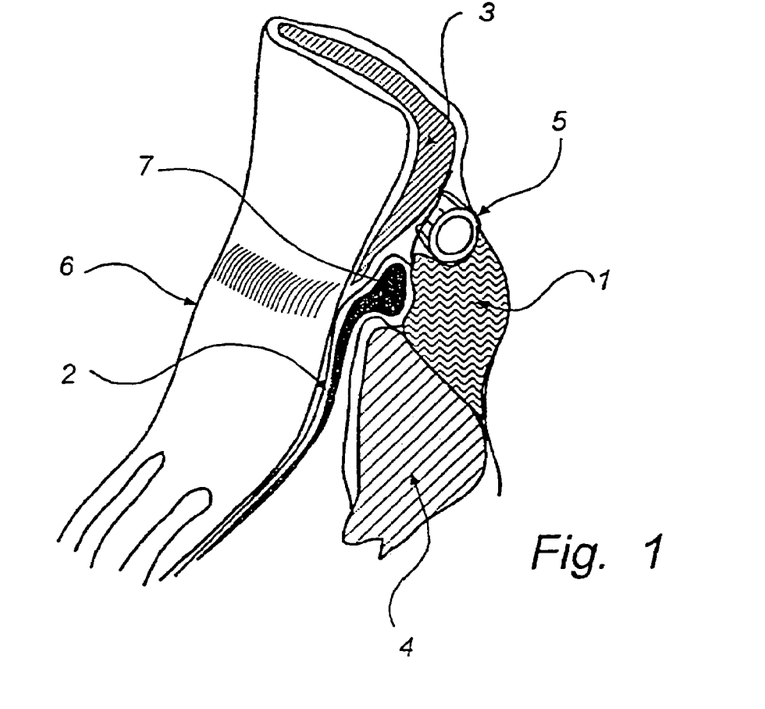
FIG. 1 is a cross-sectional view of a part of a heart.

FIG. 1 is a cross-sectional view through the heart area of the posterior atrioventricular groove 1, which is filled with fatty tissue. It shows the posterior leaflet 2 of the mitral valve and the adjoining parts 3, 4 of the atrial myocardium and the ventricular myocardium. The coronary sinus 5 is shown close to the mitral annulus 6 and behind the attachment 7 of the posterior leaflet 2. Since the coronary sinus 5 substantially encircles the mitral annulus 6, a reduction of the radius of curvature of the bent coronary sinus 5 also will result in a diameter and circumference reduction of the mitral annulus 6.

Figure 2:
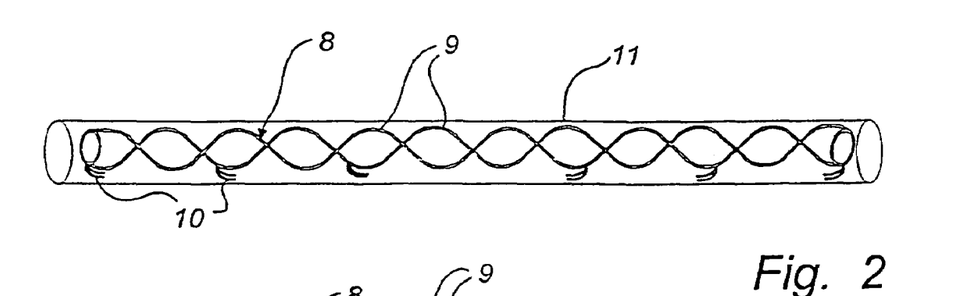
FIGS. 2 and 3 are schematic views of a first embodiment of a device according to the present invention.
Figure 3:
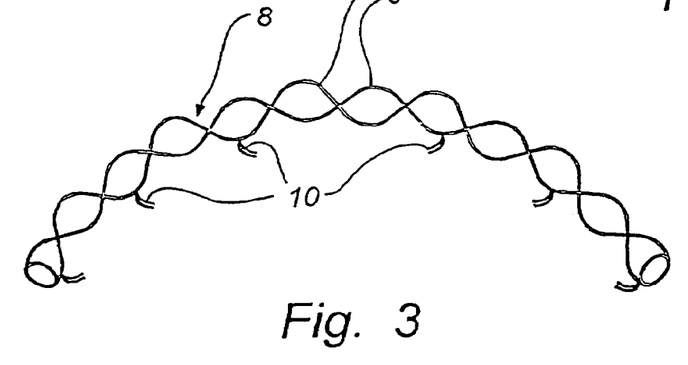

The device of FIG. 2 comprises an elongate body 8 made of memory metal, e.g. Nitinol, or other similar material which has a memory of an original shape, illustrated in FIG. 3, and can be temporary forced into another shape, illustrated in FIG. 2. This elongate body 8 comprises one, two or more memory metal strings 9 of helical or other shape so as to fit together and be able of permitting the movements described below. Along the elongate body 8 several hooks 10 are fastened so as to extend radially out therefrom. These hooks 10 are covered by a cover sheet 11 in FIG. 2.

Figure 4:
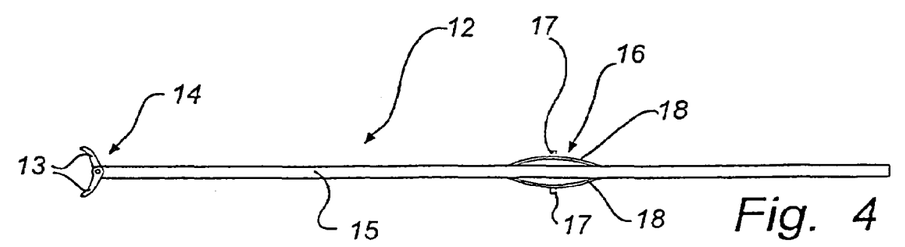
FIGS. 4–6 are schematic views illustrating an instrument, which may be used when positioning the device shown in FIGS. 2 and 3 in the coronary sinus.

The elongate body 8 is forced into a stretched or extended state by means of a stabilising instrument 12 shown in FIG. 4. This instrument 12 has two arms 13 at a distal end 14 of a rod 15 and a locking means 16 at a proximal end of the rod 15. The distance between the ends of the rod 15 corresponds to the desired length of the elongate body 8 when being inserted into the coronary sinus 5.

Figure 5:
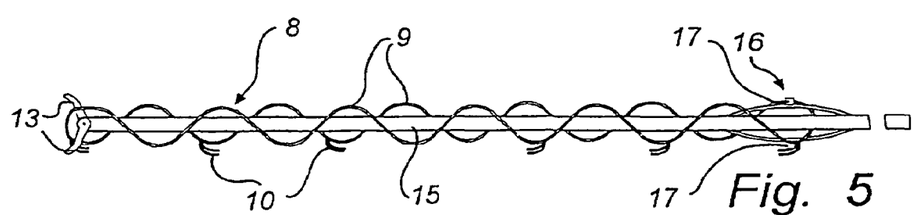
Figure 6:
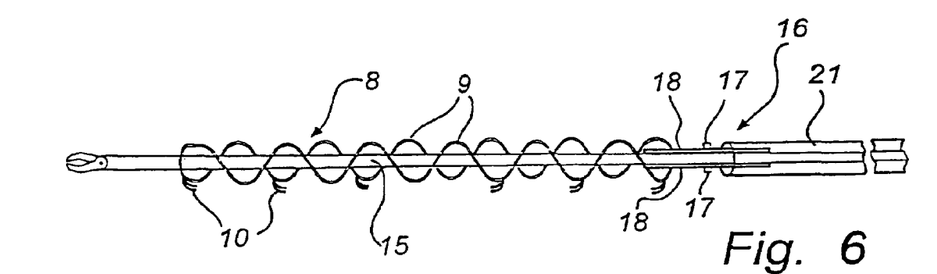

The arms 13 are free to move between the position shown in FIG. 4 and a position in alignment with the rod 15, as shown in FIG. 6. The locking means 16 has two locking knobs 17, which are pressed radially outwards from the rod 15 by two spring blades 18. Thus, the elongated body 8 can be pushed over the rod 15 of the stabilising instrument 12, then stretched between the arms 13 and the knobs 17, and finally locked in its stretched state on the stabilising instrument 12 between the arms 13 and the knobs 17, as illustrated in FIG. 5.

The rod 15 may be a metal wire which is relatively stiff between the distal end 14 and the locking means 16 but still so bendable that it will follow the shape of the coronary sinus 5. Proximally of the locking means 16 the metal wire of the stabilising instrument 11 is more pliable to be able to easily follow the bends of the veins.

The above-described elongate body 8 is positioned in the coronary sinus 5 in the following way:

An introduction sheet (not shown) of synthetic material may be used to get access to the venous system. Having reached access to the venous system, a long guiding wire (not shown) of metal is advanced through the introduction sheet and via the venous system to the coronary sinus 5. This guiding wire is provided with X-ray distance markers so that the position of the guiding wire in the coronary sinus 5 may be monitored.

Figure 8:
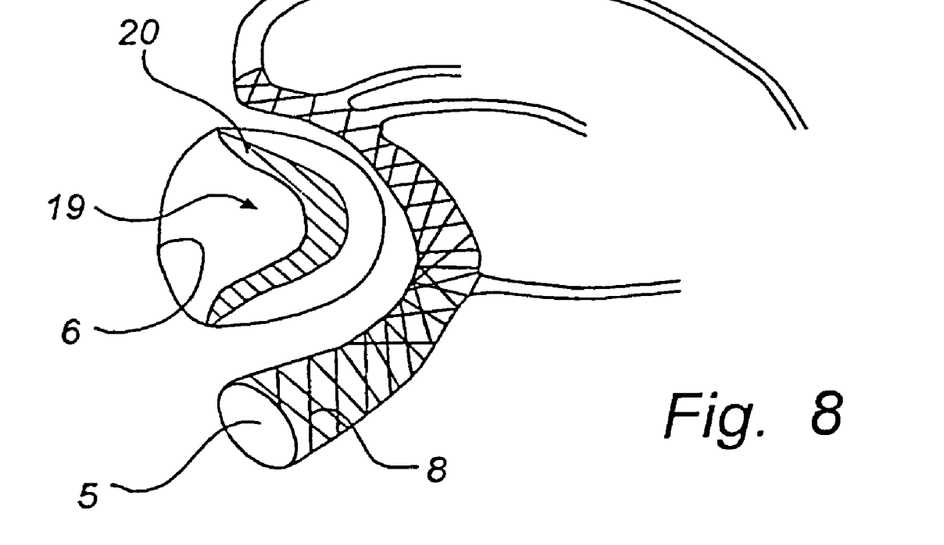
FIGS. 8 and 9 are schematic views illustrating the positioning of the device of FIGS. 2 and 3 in the coronary sinus.

The elongate body 8 is locked onto the stabilising instrument 12, as shown in FIG. 5, and introduced into the long cover sheet 11 of synthetic material. This aggregate is then pushed through the introduction sheet and the venous system to the coronary sinus 5 riding on the guiding wire. After exact positioning of the elongate body 8 in the coronary sinus 5, as illustrated in FIG. 8 where the mitral valve 19 is shown having a central gap 20, the cover sheet 11 is retracted exposing the elongate body 8 within the coronary sinus 5. This manoeuvre allows the hooks 10 on the elongate body 8 to dig into the walls of the coronary sinus 5 and into the heart. The elongate body 8 is still locked on to the stabilising instrument 12 such that the hooks 10 engage the walls of the coronary sinus 5 in the stretched or extended state of the elongate body 8.

Figure 9:
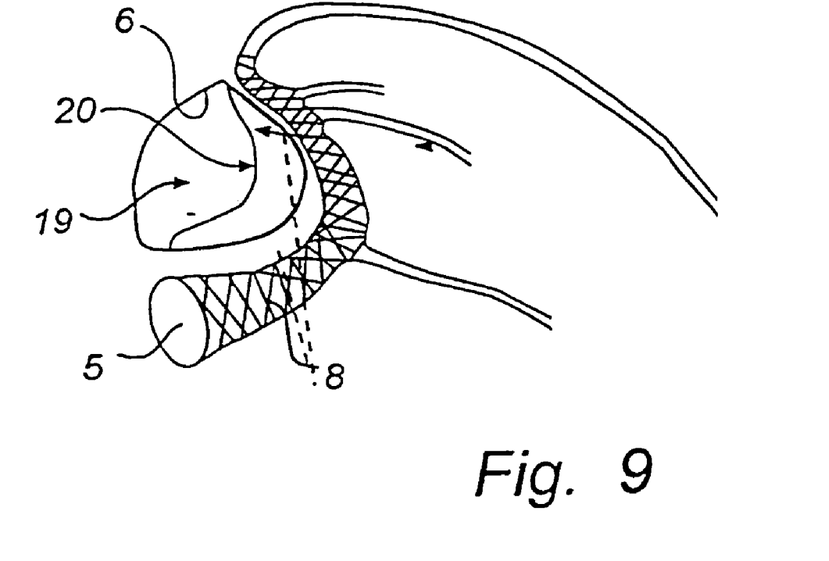

A catheter 21, shown in FIG. 6, is pushed forward on the guiding wire and the rod 15 for releasing the elongate body 8 from the locking means 16 by pressing the spring blades 18 towards the rod 15. This movement releases the knobs 17 as well as the arms 13 from engagement with the elongate body 8 which contracts as illustrated in FIG. 9 and as a result bends towards the mitral valve annulus 6 moving the posterior part thereof forward (shown by arrows in FIG. 9). This movement reduces the circumference of the mitral valve annulus 6 and thereby closes the central gap 20.

Figure 7:
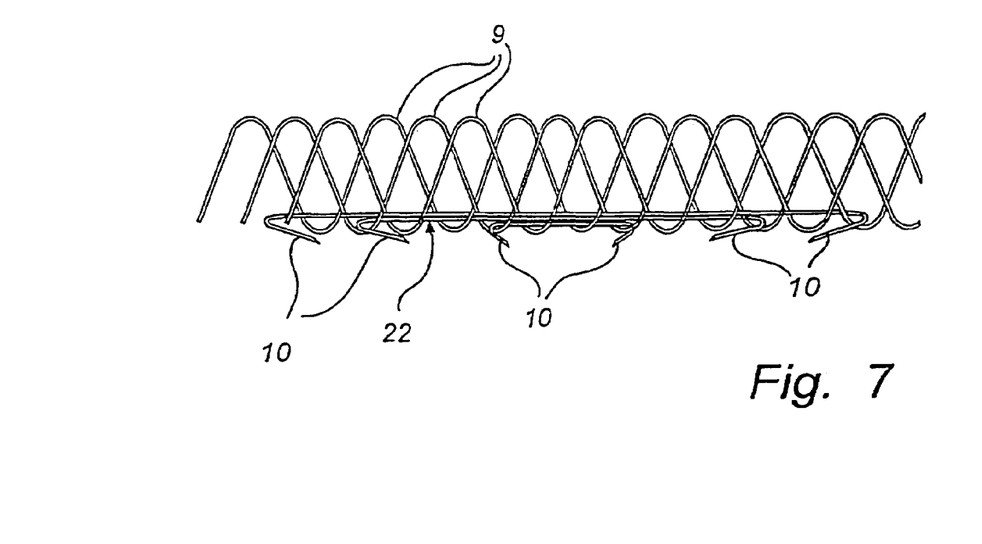
FIG. 7 is a partial, enlarged view of the first embodiment shown in FIG. 2.

FIG. 7 illustrates a part of an arrangement of the wires 9 and the hooks 10 along a peripheral part of the elongate body 8, whereby the elongate body 8 will be asymmetrically contracted resulting in a bending thereof when interconnecting parts 22 of at least some of the hooks 10 are shortened to an original shape.

Figure 10:
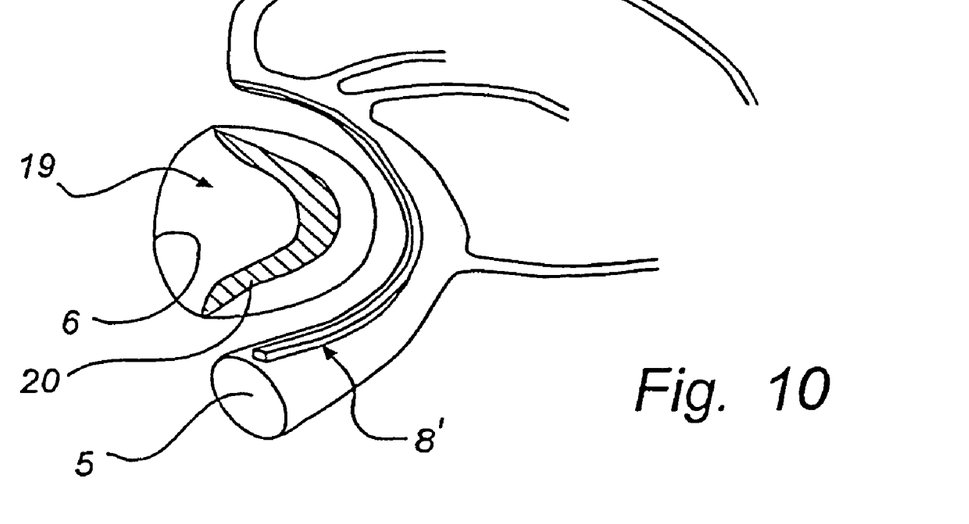
FIGS. 10 and 11 are schematic views illustrating the positioning of a second embodiment of the device according to the present invention in the coronary sinus.
Figure 11:
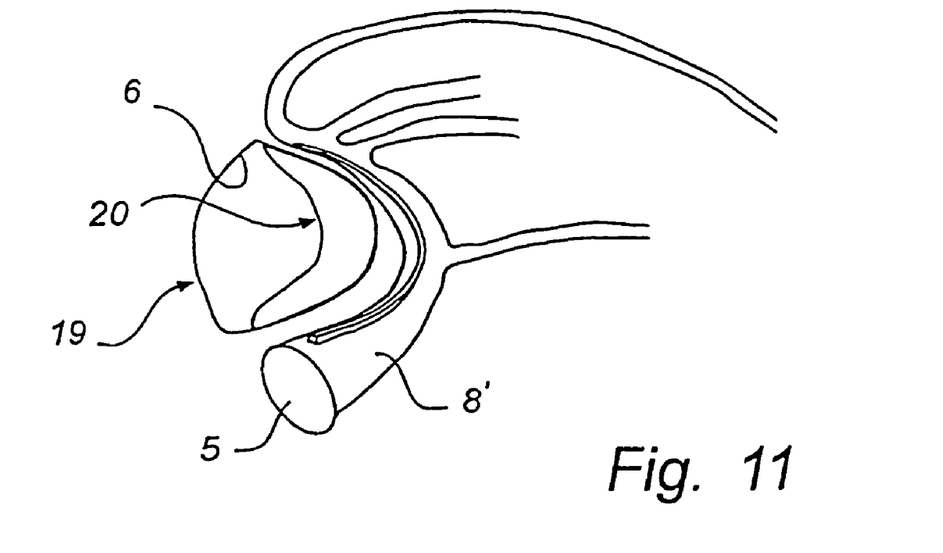

FIGS. 10 and 11 illustrate an alternative embodiment of an elongate body 8', which is a solid wire in the shape of an open U-shaped ring that will engage the wall of the coronary sinus 5 most adjacent to the mitral valve annulus 6 when inserted into the coronary sinus 5. The elongate body 8' consists of a memory metal material which when reverting to its original shape will bend as illustrated in FIG. 11. The return of the open ring 8' to its original shape may be initiated in several ways, as is obvious to the man skilled in the art.

Figure 12:
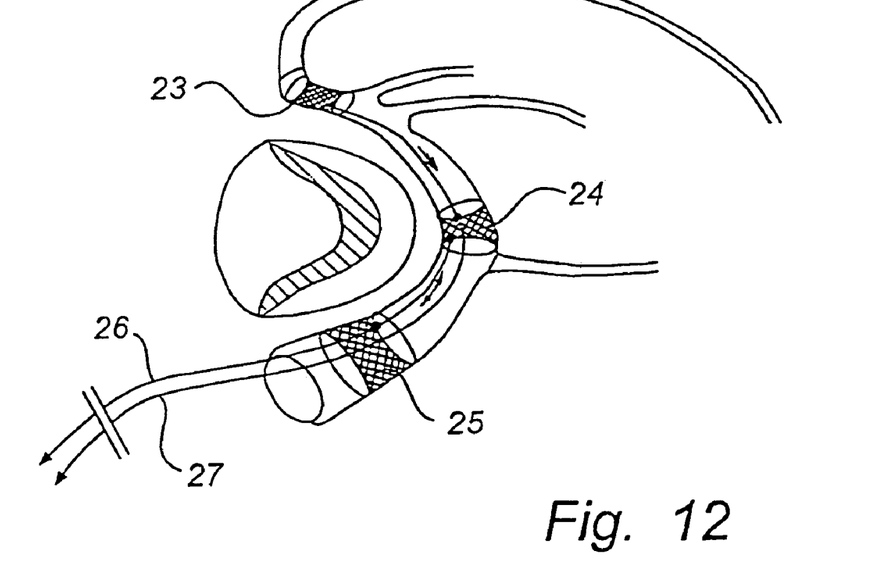
FIGS. 12 and 13 are schematic views illustrating the positioning of a third embodiment of the device according to the present invention in the coronary sinus.
Figure 13:
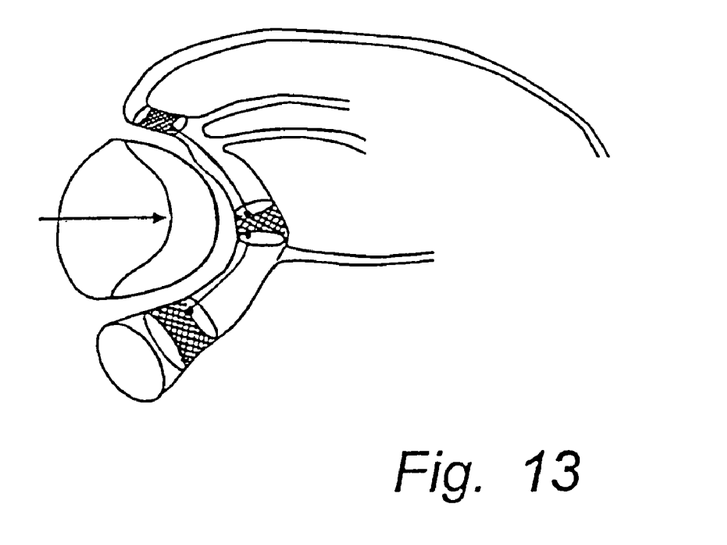

The third embodiment of the elongate body 8", illustrated in FIGS. 12 and 13, comprises three stent sections 23–25 positioned at one end of the elongate body 8", at the middle thereof and at the other end of the elongate body 8″, respectively. These stent sections 23–25 may be positioned in the coronary sinus 5 as illustrated by conventional means, such that their positions are fixed. They are connected by wires 26, 27, which may be maneuvered from outside the vein system such that the distances between the adjacent stent sections 23, 24 and 24, 25 are reduced. More specifically, these distances are reduced asymmetrically, i.e. more on the side of coronary sinus 5 most adjacent to the posterior part of the mitral valve annulus 6. Thereby, the elongate body 8″ is bent, as illustrated in FIG. 13, and presses the coronary sinus 5 against the mitral valve annulus 6 closing the gap 20.

Concludingly, the present invention provides a device placed in the coronary sinus, designed to reduce the dilatation of the mitral annulus. This device is at a distance from the attachment of the posterior leaflet that does not much exceed the distance at which present annuloplasty rings are placed by open surgery techniques, and the coronary sinus is along its entire course large enough to hold such a device. The device could be positioned by catheter technique or any other adequate technique and offers a safer alternative to the current open surgery methods. The device could be designed or heparincoated so as to avoid thrombosis in the coronary sinus, thus reducing the need for aspirin, ticlopedine or anticoagulant therapy.

It is to be understood that modifications of the above-described device and method can be made by people skilled in the art without departing from the spirit and scope of the invention.

The invention claimed is:

1. A medical apparatus for remodeling a mitral valve annulus adjacent to the coronary sinus, comprising:
    an elongate body having a proximal end region and a distal end region, each of the proximal and distal end regions dimensioned to reside completely within the vascular system, the elongate body being movable from a first configuration for transluminal delivery to at least a portion of the coronary sinus to a second configuration for remodeling the mitral valve annulus proximate the coronary sinus; and
    a forming element attached to the elongate body for manipulating the elongate body from the first transluminal configuration to the second remodeling configuration;
    wherein the elongate body is configured to press a portion of the coronary sinus against the mitral valve annulus when in the second remodeling configuration.

2. The medical apparatus according to claim 1, wherein the forming element is connected to the elongate body at a point of attachment and the forming element is movable relative to the elongate body in order to adjust the elongate body within the coronary sinus between the first and second configurations.

3. The medical apparatus according to claim 2, wherein the forming element is configured to be maneuvered from outside the vein system for manipulating the elongate body.

4. A medical apparatus as in claim 1, wherein the elongate body assumes a reduced radius of curvature when in the remodeling configuration.

5. A medical apparatus as in claim 1, further comprising a coating on the body for avoiding thrombosis in the coronary sinus.

6. A medical apparatus as in claim 1, wherein the apparatus is movable from the transluminal configuration to the remodeling configuration in response to proximal retraction of the forming element.

7. A medical apparatus as in claim 1, wherein the apparatus is movable from the implantation configuration to the remodeling configuration in response to distal advancement of the forming element.

8. A medical apparatus as in claim 1, further comprising a first stent section disposed along the distal end region of the elongate body for retaining the apparatus at a deployment site within a vessel.

9. A medical apparatus as in claim 8, wherein the first stent section is self-expanding for engaging the wall of the vessel.

10. A medical apparatus as in claim 8, wherein the forming element is connected to the first stent section.

11. A mitral valve annulus constricting device comprising a generally U-shaped member formed of resilient material and configured to assume a reduced radius of curvature after delivery into the coronary sinus for exerting a substantially radially inward force on the mitral valve annulus.

12. A method of reshaping a mitral valve annulus comprising inserting a resilient elongate body at least partially into a coronary sinus using a catheterization technique and adjusting a curvature of the elongate body within the coronary sinus for pressing the coronary sinus against the mitral valve annulus.

13. A method of closing a gap between the leaflets of a mitral valve comprising advancing a resilient elongate body at least partially into a coronary sinus using a catheterization technique and adjusting the elongate body from a location outside the body for pressing the coronary sinus against a mitral valve annulus of the mitral valve to close the gap.

14. A medical device for remodeling an extravascular tissue structure adjacent to a vessel in a patient, comprising:
    an elongate body extending between a proximal end and a distal end, and that is adjustable between a first configuration having a first shape such that the elongate body is adapted to be delivered at least in part into the vessel and a second configuration having a second shape such that the elongate body is adapted to exert a force from within the vessel onto the extravascular tissue structure in order to remodel the extravascular tissue structure,
    wherein the elongate body is adapted to be positioned in the first configuration at least in part within a coronary sinus and is adapted to remodel a mitral valve annulus adjacent to the coronary sinus when the elongate body is located at least in part within the coronary sinus and is adjusted to the second configuration; and,
    a forming element that is connected to the elongate body at a point of attachment and that is moveable in order to adjust the elongate body within the coronary sinus between the first and second configurations.

15. The medical device of claim 14 wherein the forming element is moveable relative to the elongate body in order to adjust the elongate body within the coronary sinus between the first and second configurations.

16. A medical device as in claim 14, wherein the elongate body is adjustable from the first configuration to the second configuration principally by applying a force from the forming element to the elongate body.

17. A medical device as in claim 14, wherein the elongate body is adapted to be uncoupled in the second configuration from at least a portion of the forming element located at least in part within at least the coronary sinus.

18. A medical device as in claim 14, wherein the forming element is adapted to be severed while the elongate body is positioned at least in part within the coronary sinus in the second configuration.

19. A medical device as in claim 14, wherein the proximal extension of the forming element comprises a proximal member;
the forming element further comprises a distal member that is coupled to the proximal member and is attached to the elongate body at the point of attachment;
the proximal member is adapted to transmit an applied force from outside the patient to the distal member while the elongate body along the midportion is located within the coronary sinus;
the distal member is adapted to substantially transmit the applied force from the proximal member to the elongate body in order to adjust the elongate body from the first configuration to the second configuration within the coronary sinus;
and the distal member is detachable from the proximal member while the elongate body is in the second configuration at least in part within the coronary sinus in order to thereby sever the forming element.

20. A medical device as in claim 14, wherein the forming element between the point of attachment and the proximal end portion of the elongate body is substantially circumferentially confined by the elongate body.

21. A medical device as in claim 14, wherein the forming element has a proximal extension that extends proximally from the elongate body and externally of the patient when the elongate body is located at least in part within the coronary sinus, and the elongate body within the coronary sinus is adjustable within the coronary sinus from the first configuration to the second configuration by manipulating the proximal extension outside of the patient.

22. A medical device as in claim 14, further comprising an anchor for retaining at least a portion of elongate body within the coronary sinus.

23. A medical device as in claim 14, wherein the elongate body comprises a length along an axis and is adjustable from the first configuration to the second configuration principally by transmitting an axial force from the forming element onto the elongate body relative to the axis.

24. A medical device as in claim 14, wherein the elongate body is adjustable from the first configuration to the second configuration in response to proximal retraction of the forming element.

25. A medical device as in claim 14, wherein the elongate body is movable from the first configuration to the second configuration in response to distal advancement of the forming element.

26. A device for effecting mitral valve annulus geometry of a heart comprising:
a first fixation element configured to be positioned within and fixed to the coronary sinus of the heart adjacent the mitral valve annulus within the heart;
a wire connected to the first fixation element and extending proximally from the first fixation element through the coronary sinus; and
a second fixation element configured to be positioned in and fixed in the heart proximal to the first fixation element;
wherein the wire is maneuverable from a location outside the vein system to reshape the mitral valve annulus and the first and second fixation elements are configured to hold the mitral valve annulus in a reshaped condition.

27. A method of effecting mitral valve annulus geometry in a heart, the method including the steps of:
providing an elongate body having first and second stent sections and a wire connected to the first stent section;
fixing the first stent section within the coronary sinus of the heart adjacent to the mitral valve annulus;
fixing the second stent section within the heart proximal to the first stent section; and
withdrawing the wire for pulling the first stent section toward the second stent section, thereby reshaping the coronary sinus and causing the coronary sinus to press against the mitral valve annulus.

* * * * *